United States Patent [19]

Misawa et al.

[11] Patent Number: 5,516,656
[45] Date of Patent: May 14, 1996

[54] PRODUCTION OF A NEW HIRUDIN ANALOG AND ANTICOAGULANT PHARMACEUTICAL COMPOSITION CONTAINING THE SAME

[75] Inventors: Satoru Misawa; Hitoshi Matsuda; Yoshifumi Inoue; Hideyuki Furuya, all of Toda, Japan

[73] Assignee: Nippon Mining Company, Limited, Tokyo, Japan

[21] Appl. No.: 910,528

[22] Filed: Jul. 8, 1992

Related U.S. Application Data

[62] Continuation-in-part PCT/JP91/01533, Nov. 8, 1991.

[30] Foreign Application Priority Data

Nov. 8, 1990 [JP] Japan ............................ 2-303096
Feb. 13, 1991 [JP] Japan ............................ 3-41271

[51] Int. Cl.$^6$ .................... C07K 7/10; A61K 37/64; C12N 15/15; C12N 15/70
[52] U.S. Cl. .................... 435/69.2; 435/69.1; 435/69.7; 435/252.33; 435/320.1; 530/324; 536/23.4; 536/23.5; 514/12; 930/250
[58] Field of Search ............... 435/69.1, 69.2, 435/69.7, 252.33, 320.1; 530/300, 324; 536/23.4, 23.5; 514/12; 930/250

[56] References Cited

U.S. PATENT DOCUMENTS

| | | | |
|---|---|---|---|
| 5,084,384 | 1/1992 | Wong et al. | 435/320.1 |
| 5,114,922 | 5/1992 | Maschler et al. | 530/324 |
| 5,124,261 | 6/1992 | Terada et al. | 435/320.1 |
| 5,180,668 | 1/1993 | Crause et al. | 435/69.1 |
| 5,223,407 | 6/1993 | Wong et al. | 435/320.1 |
| 5,268,296 | 12/1993 | Maschler et al. | 435/69.1 |
| 5,322,926 | 6/1994 | Tripier et al. | 530/324 |

FOREIGN PATENT DOCUMENTS

| | | |
|---|---|---|
| 0177343 | 4/1986 | European Pat. Off. . |
| 0412526 | 2/1991 | European Pat. Off. . |
| 9117250 | 11/1991 | WIPO . |

OTHER PUBLICATIONS

Braun et al., (1988) Biochemistry 27:6517–6522.
Dodt et al., "Expression, secretion and processing of hirudin in E. coli . . . ", FEBS Lett. 202(3): 373–377, Jun. 1986.
Riehl–Bellon et al, "Purification and Biochemical Characterization of Recombinant Hirudin . . . ", Biochem. 28:2941–2949, Apr. 1989.
Mao et al, "Interaction of Hirudin with Thrombin . . . " Biochem. 27:8170–8173, Oct. 1988.
Schulz et al, "Principles Of Protein Structure", pp. 14–16, 1979.

Primary Examiner—Stephen G. Walsh
Attorney, Agent, or Firm—Birch, Stewart, Kolasch & Birch

[57] ABSTRACT

Provided is a chimeric HV1/HV3 hirudin analog useful as an anti-coagulant, exhibiting higher anti-thrombin activity and less tendency to cause bleeding than hirudin HV1. Also provided are a method of producing hirudins and hirudin analogs, as well as other proteins, employing secretion vectors, and transformed microorganisms such as E. coli. Pharmaceutical compositions comprising various hirudins or the chimeric HV1/HV3 hirudin analog of the present invention and a pharmaceutically acceptable carrier are also disclosed.

10 Claims, 10 Drawing Sheets

FIG. 1

|  | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| HV1 | Val | Val | Tyr | Thr | Asp | Cys | Thr | Glu | Ser | Gly | Gln | Asn | Leu | Cys | Leu |
| HV2 | Ile | Thr | Tyr | Thr | Asp | Cys | Thr | Glu | Ser | Gly | Gln | Asn | Leu | Cys | Leu |
| HV3 | Ile | Thr | Tyr | Thr | Asp | Cys | Thr | Glu | Ser | Gly | Gln | Asn | Leu | Cys | Leu |
| HV1C3 | Val | Val | Tyr | Thr | Asp | Cys | Thr | Glu | Ser | Gly | Gln | Asn | Leu | Cys | Leu |

|  | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
|  | Cys | Glu | Gly | Ser | Asn | Val | Cys | Gly | Gln | Gly | Asn | Lys | Cys | Ile | Leu |
|  | Cys | Glu | Gly | Ser | Asn | Val | Cys | Gly | Lys | Gly | Asn | Lys | Cys | Ile | Leu |
|  | Cys | Glu | Gly | Ser | Asn | Val | Cys | Gly | Lys | Gly | Asn | Lys | Cys | Ile | Leu |
|  | Cys | Glu | Gly | Ser | Asn | Val | Cys | Gly | Gln | Gly | Asn | Lys | Cys | Ile | Leu |

|  | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|
|  | Gly | Ser | Asp | Gly | Glu | Lys | Asn | Gln | Cys | Val | Thr | Gly | Glu | Gly | Thr |
|  | Gly | Ser | Asn | Gly | Lys | Gly | Asn | Gln | Cys | Val | Thr | Gly | Glu | Gly | Thr |
|  | Gly | Ser | Gln | Gly | Lys | Asp | Asn | Gln | Cys | Val | Thr | Gly | Glu | Gly | Thr |
|  | Gly | Ser | Asp | Gly | Glu | Lys | Asn | Gln | Cys | Val | Thr | Gly | Glu | Gly | Thr |

|  | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|
|  | Pro | Lys | Pro | Gln | Ser | His | Asn | Asp | Gly | Asp | Phe | Glu | Glu | Ile | Pro |
|  | Pro | Asn | Pro | Glu | Ser | His | Asn | Asn | Gly | Asp | Phe | Glu | Glu | Ile | Pro |
|  | Pro | Lys | Pro | Gln | Ser | His | Asn | Gln | Gly | Asp | Phe | Glu | Pro | Ile | Pro |
|  | Pro | Lys | Pro | Gln | Ser | His | Asn | Gln | Gly | Asp | Phe | Glu | Pro | Ile | Pro |

|  | 61 | 62 | 63 | 64 | 65 | 66 |
|---|---|---|---|---|---|---|
|  | Glu | Glu | Tyr | Leu | Gln |  |
|  | Glu | Glu | Tyr | Leu | Gln |  |
|  | Glu | Asp | Ala | Tyr | Asp | Glu |
|  | Glu | Asp | Ala | Tyr | Asp | Glu |

FIG. 2

```
            -20         S1                                    -10       S2
        Met Lys Gln Ser Thr Ile Ala Leu Ala Leu Leu Pro Leu Leu Phe
 |AA TTC ATG AAA CAA AGC ACT ATT GCC TTG GCA |CTC TTA CCG TTA CTG TTT
   |G TAC TTT GTT TCG TGA TAA CGG AAC CGT GAG AAT GGC| AAT GAC AAA
  EcoR I                                S4
```

```
                      -1  +1
   Thr Pro Val Thr Lys Ala Val Val
   ACC CCG |GTG ACC AAA GCT GTT GT|
   TGG GGC  CAC TGG TTT CGA CAA CAT A|
            BstEII    S3          Acc I
```

FIG. 7

```
          -35                                    -10
5' -TGT  TGA CAA TTA ATC ATC GGC TCG TAT AAT GTG TGG AAT TGT GAG
   ACA   ACT GTT AAT TAG TAG CCG AGC ATA TTA CAC ACC TTA ACA CTC

S/D     EcoR I
   CGG ATA ACA ATT TCA CAC AGG AAA CAG AAT TC -3'
   GCC TAT TGT TAA AGT GTG TCC TTT GTC TTA A
```

FIG. 8

```
           -35                                     -10
5' -GGG  TGT TGA CAA TTA ATC ATC GAA CTA GTT AAC TAG TAC GCA AGT
   CCC  ACA ACT GTT AAT TAG TAG CTT GAT CAA TTG ATC ATG CGT TCA

2S/D    EcoR I
   TCA CGT AAA AAG GGT AG -3'              (TRP 1)
   AGT GCA TTT TTC CCA TCT TAA             (TRP 2)
```

FIG. 10

```
          -20                                            -10
         Met Lys Gln Ser Thr Ile Ala Leu Ala Leu Leu Pro Leu Leu Phe
 ⌐AA TTC ATG AAA CAA AGC ACT ATT GCC TTG GCA ⌐CTC TTA CCG TTA CTG TTT
 ⌐  G TAC TTT GTT TCG TGA TAA CGG AAC CGT GAG AAT GGC⌐AAT GAC AAA
  |
 EcoRI
                                       -1  +1
    Thr Pro Val Thr Lys Ala Ile Thr Tyr
    ACC CCG ⌐GTG ACC AAA GCT ATT ACG T⌐
    TGG GGC CAC T⌐G TTT CGA TAA TGC ATA⌐
                |                      |
              BstEII                  AccI
```

5,516,656

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

```
Val  Val  Tyr  Thr  Asp  Cys  Thr  Glu  Ser  Gly  Gln  Asn  Leu  Cys  Leu  Cys
 1                    5                        10                       15

Glu  Gly  Ser  Asn  Val  Cys  Gly  Gln  Gly  Asn  Lys  Cys  Ile  Leu  Gly  Ser
              20                        25                       30

Asp  Gly  Glu  Lys  Asn  Gln  Cys  Val  Thr  Gly  Glu  Gly  Thr  Pro  Lys  Pro
         35                        40                       45

Gln  Ser  His  Asn  Gln  Gly  Asp  Phe  Glu  Pro  Ile  Pro  Glu  Asp  Ala  Tyr
    50                        55                       60

Asp  Glu
65
```

( 2 ) INFORMATION FOR SEQ ID NO:2:

( i ) SEQUENCE CHARACTERISTICS:
        ( A ) LENGTH: 198 base pairs
        ( B ) TYPE: nucleic acid
        ( C ) STRANDEDNESS: double
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:2:

```
GTTGTATACA CTGATTGTAC TGAATCTGGC CAGAACCTGT GTCTGTGTGA AGGATCCAAC     60
GTTTGTGGTC AGGGTAACAA ATGTATCCTC GGGTCTGATG GTGAAAAGAA CCAGTGTGTT    120
ACTGGTGAAG GTACCCCGAA ACCGCAGTCT CATAACCAGG GTGATTTCGA ACCGATCCCG    180
GAAGACGCGT ACGATGAA                                                  198
```

( 2 ) INFORMATION FOR SEQ ID NO:3:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:3:

Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20              25                  30

Asp Gly Glu Lys Asn Gln Cys Val Thr Gly Glu Gly Thr Pro Lys Pro
        35              40                  45

Gln Ser His Asn Asp Gly Asp Phe Glu Glu Ile Pro Glu Glu Tyr Leu
    50                  55                  60

Gln
65

(2) INFORMATION FOR SEQ ID NO:4:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:4:

Ile Thr Tyr Thr Asp Cys Thr Glu Ser Gly Gln Asn Leu Cys Leu Cys
1               5                   10                  15

Glu Gly Ser Asn Val Cys Gly Lys Gly Asn Lys Cys Ile Leu Gly Ser
            20              25                  30

Asn Gly Lys Gly Asn Gln Cys Val Thr Gly Glu Gly Thr Pro Asn Pro
        35              40                  45

Glu Ser His Asn Asn Gly Asp Phe Glu Glu Ile Pro Glu Glu Tyr Leu
    50                  55                  60

Gln
65

(2) INFORMATION FOR SEQ ID NO:5:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

Ile Thr Tyr Thr Asp Cys Thr Glu Ser Gly Gln Asn Leu Cys Leu Cys
1               5                   10                  15

Glu Gly Ser Asn Val Cys Gly Lys Gly Asn Lys Cys Ile Leu Gly Ser
            20              25                  30

Gln Gly Lys Asp Asn Gln Cys Val Thr Gly Glu Gly Thr Pro Lys Pro
        35              40                  45

Gln Ser His Asn Gln Gly Asp Phe Glu Pro Ile Pro Glu Asp Ala Tyr
    50                  55                  60

Asp Glu
65

( 2 ) INFORMATION FOR SEQ ID NO:6:

( i ) SEQUENCE CHARACTERISTICS:
        ( A ) LENGTH: 75 base pairs
        ( B ) TYPE: nucleic acid
        ( C ) STRANDEDNESS: double
        ( D ) TOPOLOGY: linear ( i i ) MOLECULE TYPE: nucleic acid ( i i i ) HYPOTHETICAL: NO ( i v ) ANTI-SENSE: NO ( i x ) FEATURE:
        ( A ) NAME/KEY: -
        ( B ) LOCATION: 1..73
        ( D ) OTHER INFORMATION: /label=phoA_SIGNAL
            / note="EcoRI-AccI fragment of E. coli alkaline
            phosphatase signal peptide as shown in Figure 2."

( x i ) SEQUENCE DESCRIPTION: SEQ ID NO:6:

```
AATTCATGAA ACAAAGCACT ATTGCCTTGG CACTCTTACC GTTACTGTTT ACCCCGGTGA       60

CCAAAGCTGT TGTAT                                                        75
```

( 2 ) INFORMATION FOR SEQ ID NO:7:

( i ) SEQUENCE CHARACTERISTICS:
        ( A ) LENGTH: 77 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..72
        ( D ) OTHER INFORMATION: /label=lac_promoter
            / note="EcoRI 3'overhang as shown in Figure 7."

( x i ) SEQUENCE DESCRIPTION: SEQ ID NO:7:

```
TGTTGACAAT TAATCATCGG CTCGTATAAT GTGTGGAATT GTGAGCGGAT AACAATTTCA       60

CACAGGAAAC AGAATTC                                                      77
```

( 2 ) INFORMATION FOR SEQ ID NO:8:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..62
        ( D ) OTHER INFORMATION: /label=trp_promoter
            / note="EcoRI 3'overhang as shown in Figure 8."

( x i ) SEQUENCE DESCRIPTION: SEQ ID NO:8:

```
GGGTGTTGAC AATTAATCAT CGAACTAGTT AACTAGTACG CAAGTTCACG TAAAAAGGGT       60
```

AGAATT                                                                                       6 6

(2) INFORMATION FOR SEQ ID NO:9:

(i) SEQUENCE CHARACTERISTICS:
        (A) LENGTH: 77 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: -
        (B) LOCATION: 1..75
        (D) OTHER INFORMATION: /label=phoA_signal
            / note="EcoRI-AccI restriction fragment of E. coli
            phoA signal peptide as shown in Figure 10."

(xi) SEQUENCE DESCRIPTION: SEQ ID NO:9:

AATTCATGAA ACAAAGCACT ATTGCCTTGG CACTCTTACC GTTACTGTTT ACCCCGGTGA            6 0

CCAAAGCTAT TACGTAT                                                           7 7

PRODUCTION OF A NEW HIRUDIN ANALOG AND ANTICOAGULANT PHARMACEUTICAL COMPOSITION CONTAINING THE SAME

This application is a continuation-in-part of PCT international application No. PCT/JP91/01533 which has an international filing date of Nov. 8, 1991 which designated the United States, the entire contents of which are hereby incorporated by reference.

TECHNICAL FIELD

The present invention relates to a new hirudin analog, a DNA sequence encoding this hirudin analog, a method of manufacturing this hirudin analog using said DNA sequence, and an anti-coagulant pharmaceutical composition.

The present invention also relates to secretion vectors for foreign protein production, transformed microorganisms containing said vectors, and a method of producing hirudin or its analogs by using transformed microorganisms.

The new hirudin analog described in the present invention is useful as an anti-coagulant by virtue of its higher anti-thrombin activity and lower tendency to cause bleeding compared with known hirudin HV1.

Moreover, the secretion vectors for secretion of foreign proteins such as the hirudin analog described in the present invention facilitate the industrially advantageous production of foreign proteins such as hirudin analogs, since they enable high yield extracellular production of foreign proteins when E. coli is transformed with said vectors.

BACKGROUND ART

Hirudin is an anti-coagulation factor secreted from the salivary glands of medicinal leeches, Hirudo medicinalis, and is a mixture of peptides consisting of 65 and 66 amino acids. The structure of hirudin was determined by Dodt et al. [FEBS Lett. 165, 180(1984)] as hirudin variant 1 (HV1). Another variant, hirudin HV2, [Harvey et al., Proc. Natl. Acad. Sci. U.S.A., 83, 1084(1986)] has nine different amino acids in comparison with hirudin HV1, and still another variant, hirudin HV3, [Dodt et al., Biol. Chem. Hoppe-Seyler, 367, 803(1986)] has ten different amino acids in comparison with HV2, having the same sequence as HV2 up to $Ser^{32}$, and inserting an amino acid ($Ala^{63}$) in the C-terminal region. The structures of these three hirudin variants are shown in FIG. 1.

These natural type variants comprise 65 or 66 amino acids, and two domains are discernible. These are the spherical structured N-terminal region with three disulfide bonds, and the acidic C-terminal region exhibiting homology with the thrombin cleaving region of the pro-thrombin molecule, or with the fibrinogen cleaving region.

The present inventors have discovered that HV1 contains $Leu^{64}$-$Gln^{65}$, while HV3 contains $Asp^{65}$-$Glu^{66}$ in the C-terminal amino acid region. A patent application has been filed (Japanese Laid Open Patent Publication 3-164184 (1991)) on the synthesis of synthetic genes for HV1 and HV3 and their expression in E. coli.

Hirudin variants HV1, HV2 and HV3, having anti-thrombotic activity, are not acceptable drugs for clinical use because of their serious side effects, such as prolongation of bleeding time.

Several systems for producing hirudin by genetic engineering technology have been proposed; however, a satisfactory method has not yet been developed. From an industrial point of view, an extracellular production system is particularly desirable, since if the produced protein can be secreted extracellularly, there will be advantages not only simplifying the separation and purification of the product because of its presence in active form, but also because the product will be protected from digestion by intracellular bacterial proteases.

Methods using Bacillus subtilis, yeast or E. coli as hosts have been proposed for the production of hirudin by secretion.

Methods using Bacillus subtilis as host are disadvantageous in that plasmids are generally unstable in this bacterium, resulting in frequent curing of plasmids, making the stable protein production difficult, or the protein products in the medium are likely to be digested by their own proteases also secreted into the medium. Methods proposed for hirudin production (for example Japanese Laid Open Patent Publication 2-35084 (1990)) have not solved such problems, and the production yield is only about 100 mg/L.

In methods using yeast as hosts, it is known that the C-terminal amino acids of the products are hydrolyzed by carboxypeptidase.

In a prior report (N. Riehl-Bellon et al., Biochemistry 1989, 28, 2941–2949), by-products having 1 or 2 amino acid residues hydrolyzed off from the C-terminal end of HV2 are disclosed.

To overcome this problem, a method using carboxypeptidase-deficient yeasts (Japanese Laid Open Patent Publication 2-104279 (1990)) as hosts has been proposed, but has not led to sufficient productivity.

Using E. coli as host, a method using the alkaline phosphatase signal sequence has been reported (J. Dodt et al., FEBS Lett. 202, 373–377 (1986)). Although this is a secretion system, the product is secreted mainly into the periplasmic space, and is not satisfactory since it requires the disruption of bacterial cells by an additional recovery process step such as osmotic shock, and the product yield is as low as 4 mg/l.

DISCLOSURE OF INVENTION

The present inventors have produced various hirudin analogs based on the primary structure of the aforesaid hirudin HV1, HV2 and HV3 to compare their properties in animal models. They discovered that a hirudin analog (chimeric hirudin) having the hirudin HV1 amino acid sequence up to the 52nd amino acid and thereafter substituted with the sequence of HV3 exhibited not only high anti-thrombin activity, but also shortening of the prolongation of bleeding time.

Moreover, the present inventors have actively studied the extracellular production of foreign proteins in high yield using E. coli as host, and completed the present invention by discovering that when a replication origin (ori) of a pUC plasmid is used as a replication origin in a secretion vector with the DNA sequence for a signal peptide and a promoter, foreign protein can be secreted from E. coli in large quantity.

Therefore, the present invention relates to a new hirudin analog having high anti-thrombin activity.

Also, the present invention relates to a DNA sequence encoding the amino acid sequence of the hirudin analog having the aforesaid high anti-thrombin activity and low bleeding tendency, transformed microorganisms produced by transforming *E. coli* with expression vectors including said DNA sequence, and a method for manufacturing hirudin analogs by expressing said DNA sequence using the aforesaid transformed microorganisms, and recovering said hirudin analog.

The present invention also relates to an anti-coagulant drug having the aforesaid hirudin analog as an active ingredient.

The new hirudin analog HV1C3 of the present invention has the amino acid sequence shown in the following primary structure, SEQ ID NO:1:

| Val | Val | Tyr | Thr | Asp | Cys | Thr | Glu | Ser | Gly | (Formula-1) |
|---|---|---|---|---|---|---|---|---|---|---|
| 1 | | | | 5 | | | | | 10 | |
| Gln | Asn | Leu | Cys | Leu | Cys | Glu | Gly | Ser | Asn | |
| | | | 15 | | | | | | 20 | |
| Val | Cys | Gly | Gln | Gly | Asn | Lys | Cys | Ile | Leu | |
| | | | | 25 | | | | | 30 | |
| Gly | Ser | Asp | Gly | Glu | Lys | Asn | Gln | Cys | Val | |
| | | | | 35 | | | | | 40 | |
| Thr | Gly | Glu | Gly | Thr | Pro | Lys | Pro | Gln | Ser | |
| | | | | 45 | | | | | 50 | |
| His | Asn | Gln | Gly | Asp | Phe | Glu | Pro | Ile | Pro | |
| | | | | 55 | | | | | 60 | |
| Glu | Asp | Ala | Tyr | Asp | Glu | | | | | |
| | | | | 65 | | | | | | |

An exemplary DNA sequence encoding the amino acid sequence of this analog can be shown by the following formula, SEQ ID NO:2:

| GTT | GTA | TAC | ACT | GAT | TGT | ACT | GAA | TCT | GGC | 30 |
|---|---|---|---|---|---|---|---|---|---|---|
| CAG | AAC | CTG | TGT | CTG | TGT | GAA | GGA | TCC | AAC | 60 |
| GTT | TGT | GGT | CAG | GGT | AAC | AAA | TGT | ATC | CTC | 90 |
| GGG | TCT | GAT | GGT | GAA | AAG | AAC | CAG | TGT | GTT | 120 |
| ACT | GGT | GAA | GGT | ACC | CCG | AAA | CCG | CAG | TCT | 150 |
| CAT | AAC | CAG | GGT | GAT | TTC | GAA | CCG | ATC | CCG | 180 |
| GAA | GAC | GCG | TAC | GAT | GAA | | | | | |

The hirudin analog of the present invention shown in Formula-1 can be synthesized by chemical synthesis, or it can be produced by genetic engineering methodology.

To manufacture the hirudin analog by genetic engineering, first, as described in a later example, the hirudin HV1 secreting plasmids pMTSHV1 and pMKSHV1 were constructed and used to transform *E. coli*. Hirudin HV1 was produced by secretion using the transformed microorganisms. Plasmid pMTSHV1 comprises a promoter (Ptrp) SEQ ID NO:8, a DNA sequence encoding a signal peptide (PhoA signal) SEQ ID NO:6, a DNA sequence encoding the amino acid sequence of hirudin HV1, SEQ ID NO:3, a replication origin (ori) and a DNA sequence including a translation termination signal (rrnBT₁T₂), as shown in FIG. 3. In the present invention, in order to substitute after the 52nd amino acid of hirudin HV1 with the amino acid sequence of HV3, SEQ ID NO:5, the HV1 secreting plasmid pMTSHV1 was cleaved with a restriction enzyme to remove the DNA sequence encoding the amino acid sequence after the 52nd amino acid of hirudin HV1. On the other hand, the DNA sequence encoding the amino acid sequence beginning with the 53rd amino acid of the HV3 expression plasmid pUCHV3 was excised using a restriction enzyme. The DNA having the sequence encoding up to the 52nd amino acid of hirudin HV1 from plasmid pMTSHV1 and the DNA encoding the amino acid sequence beginning with the 53rd amino acid of hirudin HV3 derived from plasmid pUCHV3 were ligated with DNA ligase to construct the plasmid pMTSHV1C3 containing the DNA encoding the amino acid sequence of the hirudin analog of the present invention.

Plasmid pMTSHV1C3 comprises a DNA sequence including a promoter, signal peptide and replication origin (ori) derived from plasmid pMTSHV1, a DNA sequence encoding the 1st–52nd amino acids of hirudin HV1 and a translation termination signal, and a DNA sequence encoding the amino acids beginning with the 53rd amino acid of hirudin HV3 derived from plasmid pUCHV3, which is inserted between the aforesaid DNA sequence coding the 1st–52nd amino acids of hirudin HV1 and the translation termination signal.

The hirudin analog of the present invention is produced intracellularly and is secreted into the medium when plasmid pMTSHV1C3 is introduced into *E. coli*, followed by cultivation of the transformed microorganisms.

In the present invention, the hirudin analog was separated by generally known methods, and purified by methods such as column chromatography, reverse-phase HPLC, etc.

The obtained hirudin analog exhibited higher anti-thrombin activity and lower bleeding tendency compared with hirudin HV1 in the animal model. It can be formulated into an excellent anti-coagulant drug by preparing it by generally known methods of formulation. In other words, the hirudin analog of the present invention can be further prepared by any common methods using any common carriers for pharmaceutical use or additives for formulation. The pharmaceutical composition can be administered intravenously, intracutaneously, subcutaneously intramuscularly, or non-orally topically. Although the proper dose will be determined for each case by considering factors such as the symptoms, age and sex of patient, it is generally in the range of 0.1 mg to 100 mg for an adult per day, and the total amount will be administered in one to several doses.

Moreover, as previously described, the present invention is also related to secretion vectors for foreign protein production, particularly to the secretion vector for high yield extracellular production of hirudin or its analog.

Also, the present invention is related to secretion vectors containing DNA sequences encoding hirudin or its analogs, microorganisms (*E. coli*) transformed with said secretion vectors, and methods of manufacturing hirudin or its analogs by culturing said transformed microorganisms and recovering the product from the medium.

The foreign protein secretion vector of the present invention comprises a replication origin (ori) derived from a pUC plasmid, a tac promoter or trp promoter, a signal peptide sequence and a DNA sequence encoding foreign protein.

The DNA fragment containing the replication origin (ori) of a pUC plasmid in the present invention can be prepared by cleaving commercially available pUC family plasmids, for example, pUC9, pUC18 or pUC19, with combinations of suitable restriction enzymes. For example, a DNA fragment of about 1440 base pairs, including a replication origin (ori) prepared by cleaving pUC18 with restriction enzymes Pvu I, or Pvu I and Pvu II, can be used as a pUC replication origin in the plasmids of the present invention.

The tac promoter and trp promoter of the present invention have the nucleotide sequences shown in FIGS. 7 and 8, SEQ ID NO: 7 and SEQ ID NO:8, respectively, and can be easily synthesized by a DNA synthesizer, etc. Therefore, these promoters can be synthesized and ligated with fragments containing the replication origin (ori) of plasmid pUC18. Alternatively, they can be relatively easily prepared by ligating DNA fragments generated by cleaving commercially available plasmids with restriction enzymes. For example, plasmid pMK2 can be prepared using T4 DNA ligase by ligating DNA fragments including the DNA sequence of the tac promoter obtained by cleaving the commercially available plasmid pKK223-3 (Pharmacia) with restriction enzymes Pvu I and Nru I and a DNA fragment including a replication origin (ori) obtained by cleaving the commercially available plasmid pUC18 with restriction enzymes Pvu I and Pvu II.

Plasmid pMT1 can be prepared by removing the fragment including the DNA sequence of the tac promoter by cleaving the abovementioned plasmid pMK2 with restriction enzymes EcoRI and Eco47III, and then inserting a fragment including the trp promoter sequence synthesized by a DNA synthesizer.

For the DNA sequence of the signal peptides of the present invention, DNA sequences coding signal peptides of proteins localizing in the periplasm of *E. coli* can be used, for example enzymes such as alkaline phosphatase (pho A) and B-lactamase (bla), or outer-membrane proteins such as OmpA, OmpB and OmpF. These DNA fragments can easily be prepared using a DNA synthesizer.

Although any protein can be the foreign protein encompassed by the present invention, hirudin and its variants are particularly suitable. The amino acid sequences of these proteins are shown in FIG. 1 as hirudins HV1, HV2, HV3 and HV1C3.

BRIEF DESCRIPTION OF THE DRAWINGS

FIG. 1 shows the amino acid sequence of hirudins HV1, HV2, HV3, and HV1C3, SEQ IDs NOs: 3, 4, 5, and 1, respectively.

FIG. 2 shows the DNA sequence of the phoA signal peptide, SEQ ID NO:6.

FIG. 6(B) shows the C4 reverse phase HPLC profile of hirudin HV1C3, respectively.

FIG. 7 shows the DNA sequence of the tac promoter used in the present invention, SEQ ID NO:7.

FIG. 8 shows the DNA sequence of the trp promoter used in the present invention, SEQ ID NO:8.

FIG. 10 shows the DNA sequence of the signal peptide PhoA for hirudin HV3 secretion used in the example 5, SEQ ID NO:9.

BEST MODE FOR CARRYING OUT THE INVENTION

The procedures for constructing plasmids pUCHV1, pMT1 and pMK2 for use in constructing pMTSHV1 or pMKSHV1 as hirudin HV1 secretion plasmids used in the present invention, and of plasmid pUCHV3 for use in constructing plasmid pMTSHV1C3, are provided in the following reference examples.

[Reference example 1]

Preparation of plasmid pUCHV1 and plasmid pUCHV3

10 μg of commercially available plasmid pUC18 was digested with 30 units of EcoRI and 30 units of HindIII at 37° C. for 2 hours. The vector moiety was then separated by agarose gel electrophoresis followed by extraction. Proteins were removed by phenol extraction; DNA was precipitated with cold ethanol and dissolved in 50 μl of TE buffer solution (10 mM Tris-HCl. pH8.0, 1 mM EDTA). To this amount of solution which should contain 50 ng of DNA, 10 μl of 66 mM Tris-HCl, pH7.5, 5 mM $MgCl_2$, 5 mM DTT, 1 mM ATP, and 300 units of T4 DNA ligase containing double stranded HV1 or HV3 DNA was added, followed by reaction overnight at 16° C. to generate plasmid pUCHV1 or pUCHV3, in which the HV1 gene or HV3 gene was inserted, respectively, between the EcoRI and HindIII sites of plasmid pUC18.

[Reference example 2]

Preparation of plasmid pMK2 and plasmid pMT1

(a) preparation of plasmid pMK2

A fragment containing the tac promoter which was obtained by cleaving commercially available plasmid pKK223-3 (Pharmacia) with the restriction enzymes PvuI and NruI, a fragment containing a replication origin (ori) obtained by cleaving commercially available pUC18 with restriction enzymes PvuI and PvuII, and a fragment containing the ampicillin resistance gene were ligated using T4 DNA ligase. The thus obtained fragment was introduced into *E. coli* JM109, followed by culturing, screening for ampicillin resistance, and a vector having both the tac promoter and the replication origin (off) of pUC18 was obtained, and designated as pMK2.

(b) Preparation of plasmid pMT1

10 μg of plasmid pMK2 was digested with 30 units of EcoRI and Eco47III, removing the fragment containing the tac promoter, and then the fragment containing the replication origin (ori) was recovered by agarose gel electrophoresis. The DNA fragment containing the trp promoter was synthesized by a DNA synthesizer. This fragment was ligated with the aforesaid fragment generated by digesting pMK2 with EcoRI and Eco47III, using T4 DNA ligase at 16° C. overnight. The ligation products were used to transform *E. coli* JM109 to prepare a vector having both the trp promoter and the replication origin (ori) of plasmid pMK2. The DNA sequence of this plasmid was confirmed by the method of Sanger et al., and designated as pMT1.

The present invention is shown in detail hereinafter via the following Example.

EXAMPLE 1

(1) Construction of hirudin HV1 secretion plasmid pMTSHV1

Figure 3:
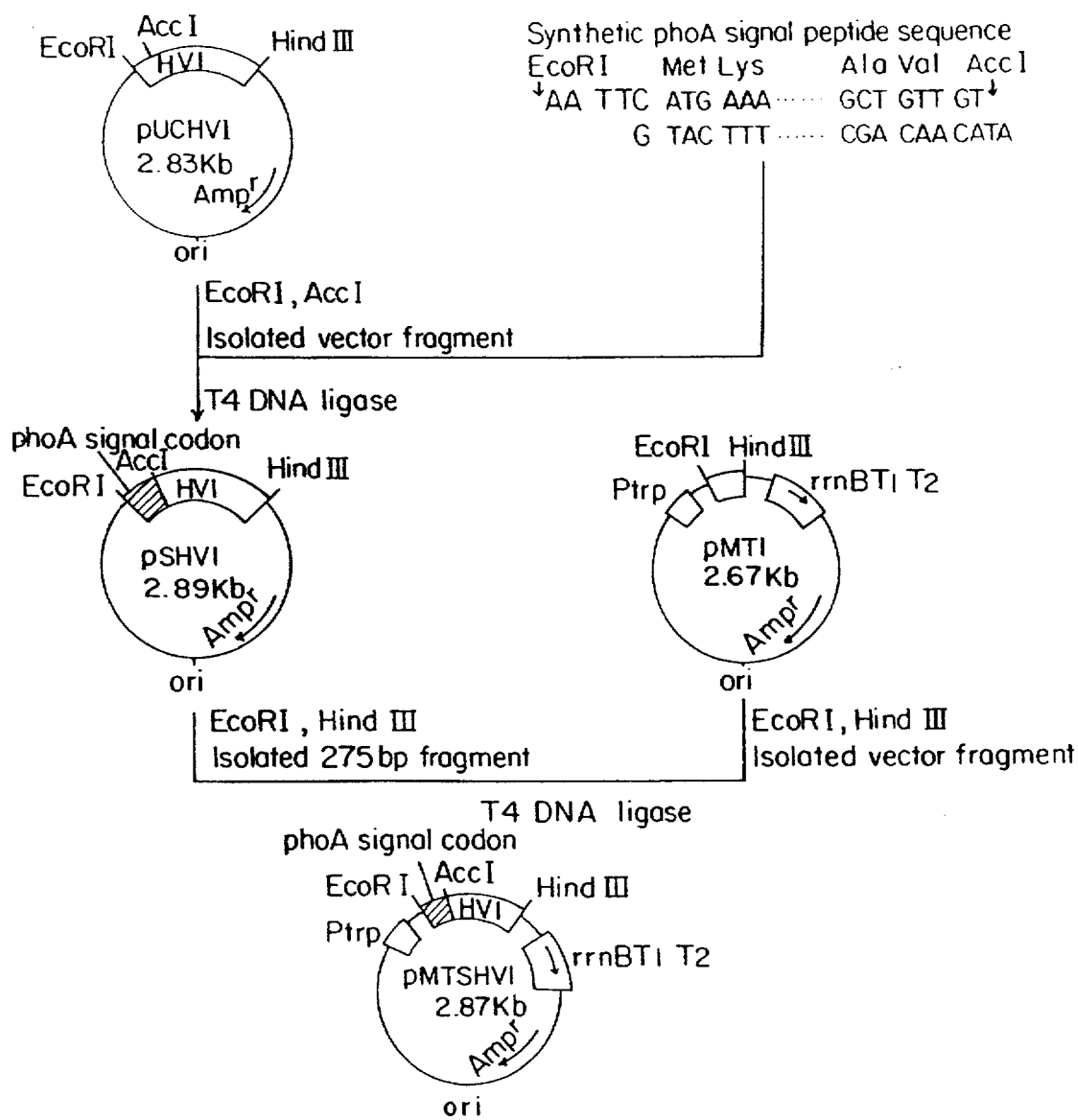
FIG. 3 shows an outline of the construction of hirudin HV1 secreting plasmid pMTSHV1.

Plasmid pMTSHV1 was constructed according to the procedure shown in FIG. 3. Four oligonucleotides indicated in FIG. 2 were synthesized to construct a DNA fragment corresponding to the signal peptide of alkaline phosphatase (phoA) of *E. coli* and the DNA fragment encoding $Val^1$-$Val^2$ of the N-terminal amino acid of hirudin HV1. After deprotection, each oligonucleotide was purified by 10% polyacrylamide gel electrophoresis.

After 500 pmol of each of the two oligonucleotides S2 and S4 were phosphorylated, 20 pmol each of the 4 oligonucleotides were mixed, annealed and then treated at 16° C. overnight in 20 μl solution containing T4 DNA ligase. After removal of protein using phenol and chloroform, and precipitation by cold ethanol, the desired double stranded DNA fragment was obtained. 1/10 the amount of the obtained fragment and 100 ng of plasmid pUCHV1 (Japanese Laid Open Patent Publication 3-164184 (1991)) cleaved with restriction enzymes EcoRI and AccI were reacted with T4 DNA ligase at 16° C. overnight. Hybrid plasmid pSHV1, containing the fusion gene in which the DNA sequence encoding hirudin HV1 is ligated immediately after the sequence encoding the phoA signal peptide, was obtained by transforming E. coli JM109. The DNA sequence of this plasmid pSHV1 was confirmed by the method of Sanger et al.

10 μg of pSHV1 was digested with restriction enzymes EcoRI (30 units) and HindIII (30 units), and the 276 bp fused gene fragment was purified by agarose gel electrophoresis.

100 ng of the obtained DNA fragment and 100 ng of DNA prepared by digesting E. coli expression vector pMT1 (Japanese Laid Open Patent Publication 3-76579 (1991)) with restriction enzymes EcoRI and HindIII, followed by purifying the DNA fragments by agarose gel electrophoresis, were ligated using T4 DNA ligase at 16° C. overnight. The resulting reaction mixture was used to transform E. coli JM109 to obtain the hirudin HV1 secretion plasmid pMTSHV1, in which the fused gene encoding the phoA signal peptide and hirudin HV1 is follows trp promoter region. The DNA sequence of pMTSHV1 was confirmed by the method of Sanger et al.

(2) Construction of the hirudin HV1 secreting plasmid pMKSHV1

Figure 4:
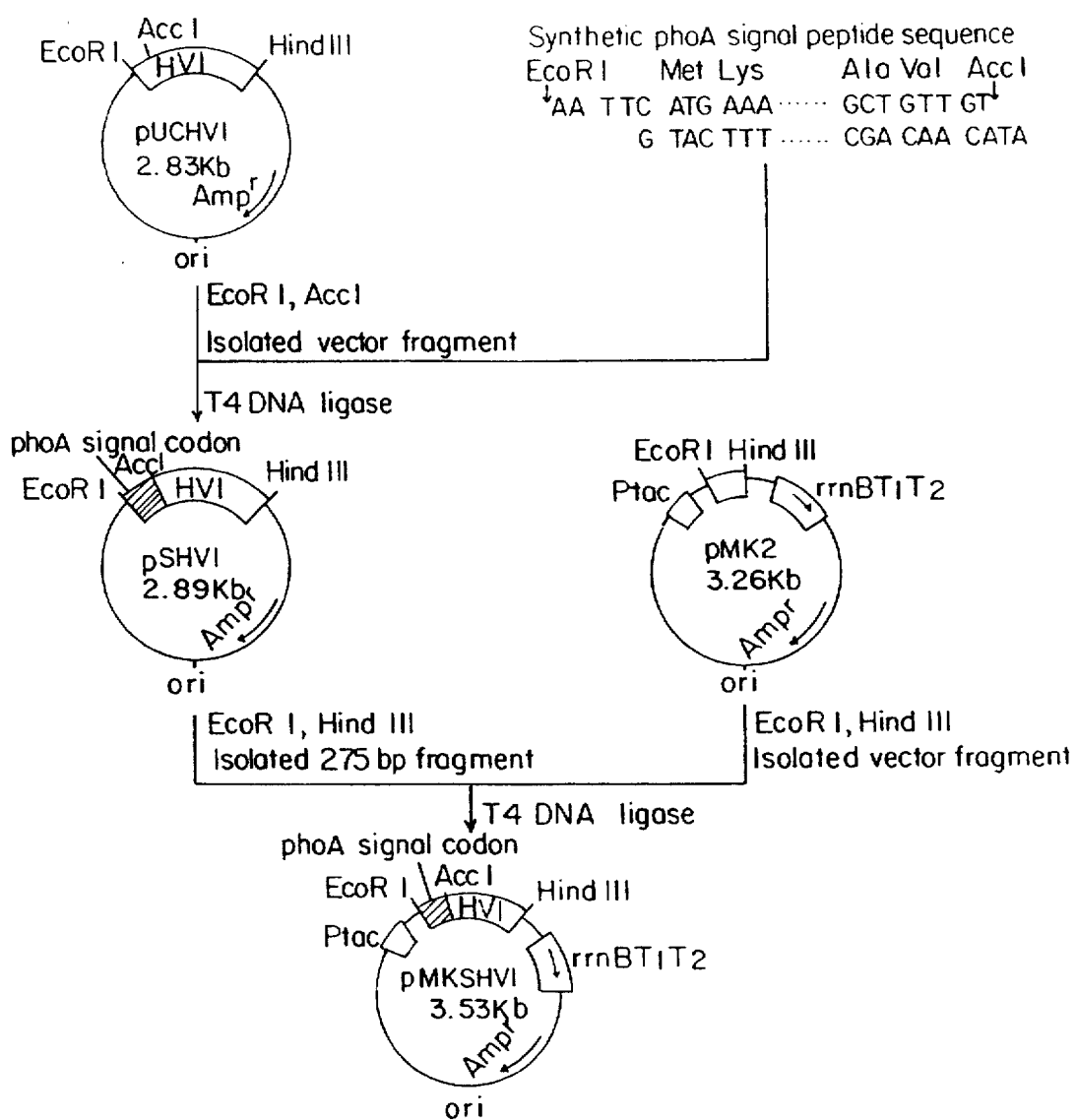
FIG 4 shows an outline of the construction of plasmid pMKSHV1.

Plasmid pMKSHV1 was constructed according to the method shown in FIG. 4.

The aforesaid fused DNA encoding the phoA signal peptide and hirudin HV1, and the DNA fragment obtained by digesting E. coli expression plasmid pMK2 (Japanese Laid Open Patent Publication 3-76579 (1991)) with restriction enzymes EcoRI and HindIII, were ligated using T4 DNA ligase; the ligation products were used to transform E. coli JM109, and the hirudin HV1 secreting plasmid pMKSHV1 having the fused gene inserted downstream of the tac promoter was obtained. The DNA sequence of plasmid pMKSHV1 was confirmed by the method of Sanger et al.

(3) Secretion production of hirudin HV1 by pMTSHV1

E. coli JM109 transformed with plasmid pMTSHV1 or pMKSHV1, constructed in (1) and (2) above, was cultured in 2×YT medium (16 g/l bactotryptone, 10 g/l bacto-yeast extract and 5 g/l NaCl) containing 100 μg/ml of ampicillin. After culturing at 37° C. for 24 hours, 1 ml of culture medium was collected.

Precipitated cells of each sample were suspended in 1 ml of 50 mM Tris-HCl (pH7.5) containing 25% sucrose and 1 mM EDTA, followed by incubation at room temperature for 10 minutes. After collecting the cells by centrifugation at 6,000×g for 10 minutes, the cells were suspended in 1 ml of cold water to release the substances in the periplasmic space by osmotic shock. Cells were removed from the periplasmic fraction by centrifugation at 6,000×g for 10 minutes. The amount of secreted and periplasmically-accumulated hirudin was determined by measuring the anti-thrombin activity in the supernatant. The antithrombin activity is based on quantitative measurement of the color intensity generated by thrombin's hydrolytic activity on the synthetic chromogenic substrate chromozyme TH (Tocylglycil-prolylarginine-4-nitroanilideacetate, Boeringer-Mannheim) and hirudin's inhibitory activity against thrombin, which will repress color generation.

This reaction was carried out as follows. In the 1 ml of said reaction volume, 0.36 NIH U of human-thrombin (Sigma) were added to buffer containing 100 mM Tris-HCl (pH8.5), 150 mM NaCl and 0.1% polyethyleneglycol-6000, followed by addition of standard hirudin or unknown sample, and followed by pre-incubation at 37° C. for 3 minutes.

Both the substrate and chromozymeTH were added to a final concentration of 200 μM to measure the release of p-nitroanilide by the increase of absorbance at 405 nm of the solution per 1 minute, and the anti-thrombin activity (ATU) was calculated.

As a result, the strain harboring plasmid pMTSHV1 exhibited 450 ATU of anti-thrombin activity per 1 ml of the culture medium. The strain harboring plasmid pMKSHV1 exhibited 360 ATU of anti-thrombin activity per 1 ml of the culture medium. Results of further studies on the production of hirudin with various E. coli strains such as JM101, JM103, JM109, TG1, HB101, JA221, IFO3301, C600, RR1 and DH5 in which plasmid pMTSHV1 was introduced by the transformation method of Hanahan et al. are shown in Table 1.

When RR1 was used as host, about 2000 ATU/ml of HV1 was produced extracellularly.

TABLE 1

| Bacterial species | A660 nm | Activity (ATU/ml) | Activity of produced HV1 (ATU/ml/A660 nm) |
|---|---|---|---|
| JM101 | 4.12 | 256.4 | 62.2 |
| JM103 | 4.12 | 306.7 | 74.4 |
| JM109 | 3.06 | 450.5 | 147.2 |
| TG1 | 5.77 | 185.2 | 32.1 |
| HB101 | 3.76 | 99.0 | 26.3 |
| JA221 | 5.72 | 413.2 | 72.2 |
| IFO3301 | 2.61 | 148.1 | 56.8 |
| C600 | 4.02 | 526.3 | 130.9 |
| RR1 | 7.23 | 2000.0 | 276.6 |
| DH5 | 7.00 | 10.6 | 1.5 |

(4) Secretion of hirudin HV1 into the culture medium by transformed E. coli JM109/pMTSHV1

When E. coli strain JM109 was transformed with plasmid pMTSHV1 (E. coli JM109/pMTSHV1) (FERM BP-3266) and cultured in 2 L of 2×YT culture medium containing 2% glucose in a 5 L fermenter with agitation and aeration at 37° C. for 24 hours, about 5300 ATU per 1 ml of hirudin HV1 were produced extracellularly.

(5) Purification of hirudin HV1 from culture media

After fermentation, 1.5 L of culture medium were collected and centrifuged at 6,000×g for 10 minutes to separate supernatant from cellular debris. Since the salt concentration of the supernatant was 1.3% when it was measured with a salt meter, the supernatant was diluted 4-fold with 10 mM potassium phosphate buffer (pH7.0) and filtered through a 3.2 μm filter (Pole Co. Ltd). The filtrate was loaded on a QAE-toyopearl column (4.4×7 cm) equilibrated with 10 mM potassium phosphate buffer (pH7.0). After loading the sample, the column was equilibrated in buffer, followed by stepwise elution of hirudin HV1 with 0.2M NaCl. The eluted solution was concentrated using an Amicon Diaflow membrane (YM5), followed by gel filtration on Sephacryl S-100HR pre-equilibrated with 10 mM potassium phosphate buffer (pH7.0) for desalting.

The active fractions were loaded on a column of DEAE-toyopearl (4.4×40 cm) equilibrated with 10 mM potassium phosphate buffer (pH7.0), washed thoroughly, and then eluted with a linear gradient created between 3 L of the equilibration buffer and 3 L of 0.3M NaCl in equilibration buffer. Final purification was carried out on a C4 reverse phase HPLC column with Delta-prep 3000, which is a Waters' product. The purified hirudin HV1 was obtained by eluting it from the column using a linear gradient of 15 to 30% (v/v) acetonitrile containing 0.065% (v/v) trifluoroacetate.

The degree of purification at each step is shown in Table 2.

TABLE 2

| Purification step | Total protein (mg) | Total activity (ATU) | relative activity (ATU/mg) | recovery (%) |
| --- | --- | --- | --- | --- |
| culture medium | 13680 | 6030297 | 441 | 100 |
| QAE-toyopearl | 1324 | 6132812 | 4630 | 101.7 |
| S-100HR | 872 | 6162156 | 7066 | 102.2 |
| DEAE-toyopearl | 821 | 6080019 | 7407 | 100.8 |
| C4RP-HPLC | 570 | 4675211 | 8202 | 77.5 |

The amino acid composition of the thus obtained hirudin HV1 exhibited a value consistent with that of natural hirudin HV1 as shown in Table 3. The N-terminal amino acid sequence of purified hirudin HV1 started with Val-Val-Tyr as shown in Table 4, indicating that correct cleavage of the phoA signal peptide had occurred. The anti-thrombin activity was 8202 ATU/mg.

TABLE 3

|  | HV1 | HV1C3 |
| --- | --- | --- |
| Asx | 9.00 | 9.95 |
| Thr | 3.86 | 3.84 |
| Ser | 3.70 | 3.67 |
| Glx | 13.78 | 12.65 |
| Gly | 8.89 | 8.86 |
| Ala | 0.00 | 1.06 |
| Cys | 5.40 | 5.40 |
| Val | 2.94 | 2.92 |
| Met | 0.00 | 0.00 |
| Ile | 1.89 | 1.86 |
| Leu | 4.04 | 3.01 |
| Tyr | 2.06 | 2.06 |
| Phe | 1.00 | 1.00 |
| His | 1.13 | 1.11 |
| Lys | 3.02 | 3.02 |
| Arg | 0.00 | 0.00 |
| Pro | 3.05 | 4.09 |

TABLE 4

| Cycle number | Amino acid | Yield (pmol) |
| --- | --- | --- |
| 1 | Val | 310 |
| 2 | Val | 490 |
| 3 | Tyr | 189 |
| 4 | Thr | 138 |
| 5 | Asp | 42 |
| 6 | Cys | — |
| 7 | Thr | 44 |
| 8 | Glu | 99 |
| 9 | Ser | 436 |
| 10 | Gly | 205 |
| 11 | Gln | 131 |
| 12 | Asn | 66 |
| 13 | Leu | 148 |
| 14 | Cys | — |

TABLE 4-continued

| Cycle number | Amino acid | Yield (pmol) |
| --- | --- | --- |
| 15 | Leu | 174 |

(6) Preparation of chimeric hirudin HV1C3 secretion plasmid pMTSHV1C3

Figure 5:
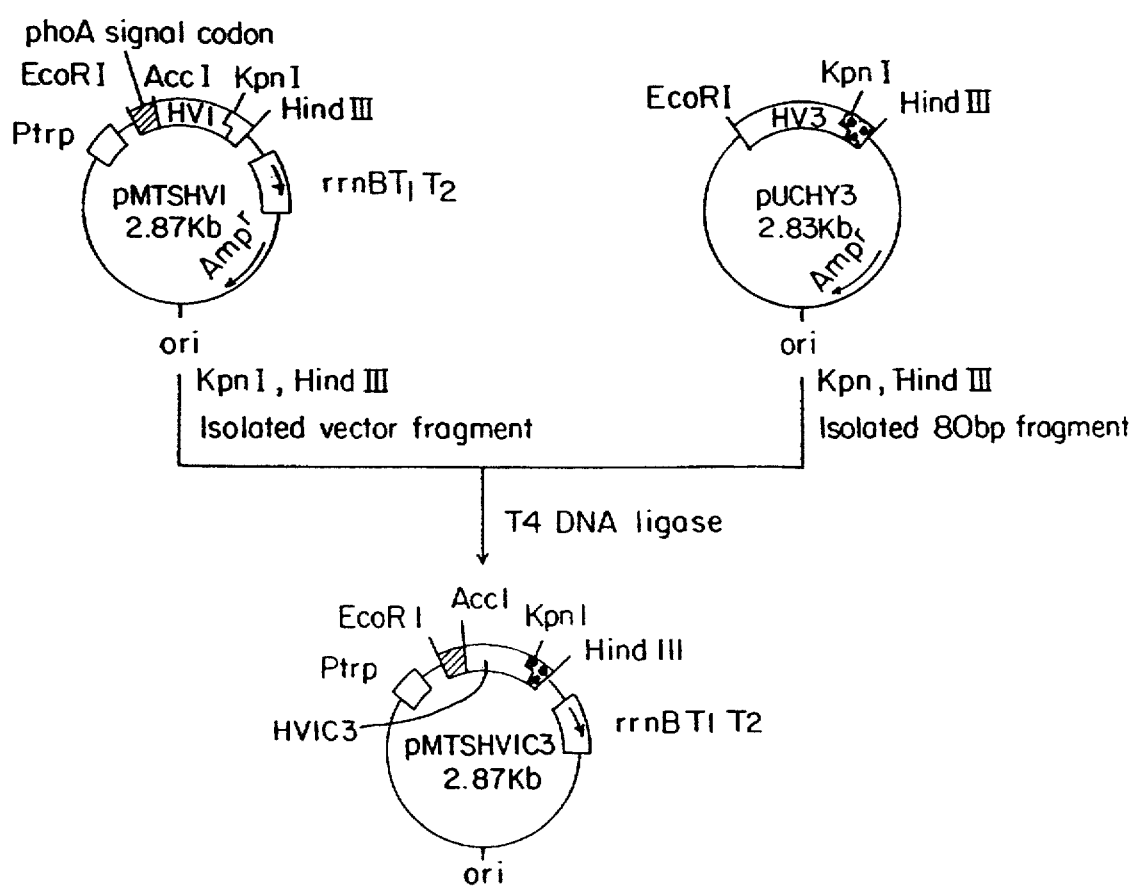
FIG. 5 shows an outline of the construction of hirudin HV1C3 secreting plasmid pMTSHV1C3.

Plasmid pMTSHV1C3 was constructed according to the procedure described in FIG. 5. To substitute after the 52nd amino acid of hirudin HV1 with the sequence of HV3, the HV1 secretion plasmid pMTSHV1 (10 µg) was digested with restriction enzymes Kpn I (30 units) and Hind III (30 units), followed by agarose gel electrophoresis to purify a DNA fragment of 2.8 Kbp.

Similarly, 10 µg of plasmid pUCHV3 (Japanese Laid Open Patent Publication 3-164184 (1991)) was also digested with Kpn I and Hind III, and an 80 bp DNA fragment encoding the C-terminal amino acid sequence of HV3 was purified.

100 ng of both DNA fragments were reacted with T4 DNA ligase at 16° C. overnight, and the resulting reaction mixture was used to transform E. coli JM109 to obtain chimeric hirudin HV1C3 secretion plasmid pMTSHV1C3. The DNA sequence of plasmid pMTSHV1C3 was confirmed by the method of Sanger et al.

(7) Production of chimetic hirudin HV1C3 by secretion using hirudin secretion plasmid pMTSHV1C3

E. coli RR1 (FERM BP-3130) transformed with plasmid pMTSHV1C3 which was constructed in (6) above was cultured in 2×YT medium containing 100 µg/ml of ampicillin. After culturing at 37° C. for 24 hours, 1 ml of culture medium was collected, and osmotic shock was applied in order to measure the anti-thrombin activity of the periplasmic fraction.

As a result, 3060 ATU of anti-thrombin activity per 1 ml of culture medium was detected.

(8) Secretion of chimeric hirudin HV1C3 into the fermentation or culture medium by transformed strain E. coli JM109/pMTSH1C3

When E. coli JM109 (FERM BP-3104) transformed with plasmid pMTSHV1C3 was cultured in 2 L of 2×YT culture medium containing 2% glucose in a 5 L fermenter with agitation and aeration at 37° C. for 24 hours, a total anti-thrombin activity of 6050 ATU/ml, 350 ATU/ml in the periplasm, and 5700 ATU/ml in the culture medium, was detected.

(9) Purification of chimeric hirudin HV1C3

Figure 6A:
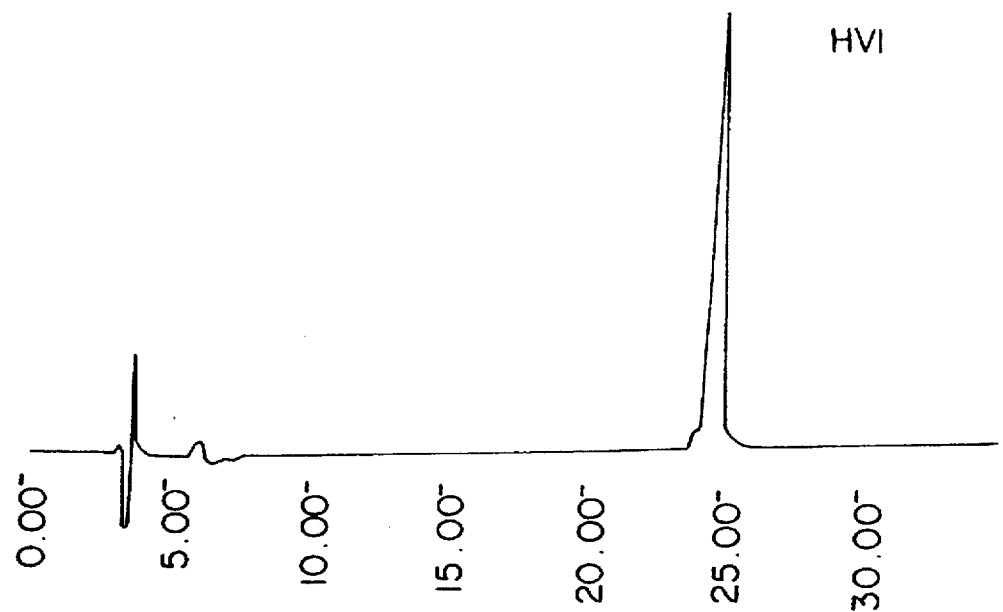
FIG. 6(A), FIG. 6(B) FIG. 6(A) shows the C4 reverse phase HPLC profile of hirudin HV1.
Figure 6B:
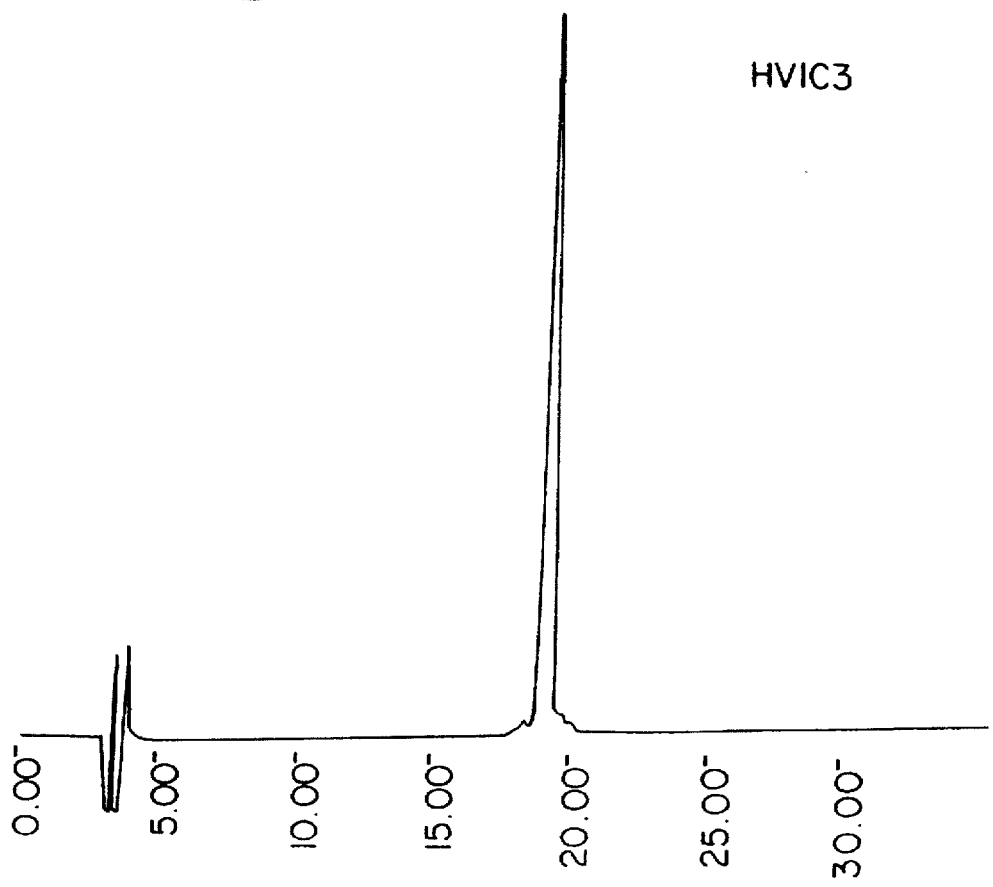

Hirudin HV1C3 was purified from the culture medium obtained in (8) above according to the method in (5) above. When the amino acid sequence of purified chimeric hirudin HV1C3 was determined, the C-terminal amino acid sequence was confirmed to be different from HV1, as designed, as shown in FIG. 1. The specific activity was 11,250 ATU/mg. The HPLC profiles of purified HV1 and HV1C3 are shown in FIG. 6. The experiment was carried out with a VYDAC C4 (0.46×25 cm) column using a linear gradient of acetonitrile from 15 to 30% at a flow rate of 1 ml/min for 30 minutes.

EXAMPLE 2

Inhibitory action of hirudin against thrombin induced death

Thrombin (10 NIH unit/10 g) was administered intravenously to male mice (20–25 g), without anesthesia, and the anti-thrombin activity of the tested compound was evaluated by observing the disappearance of roll over reflection and death as indexes. All the tested compounds were dissolved in saline, and 0.05 ml/10 g were administered intravenously 5 min prior to the thrombin injection. The results are shown in Table 5.

TABLE 5

Inhibitory action of hirudin against thrombin-induced death

| Tested compound | Amount administered (μg/10 g weight) | Score* |
|---|---|---|
| Thrombin + Saline (10 NIH unit/10 g weight) | | 1.7 |
| Thrombin + HV1 (10 NIH unit/10 g weight) | 100 | 1.3 |
| | 200 | 0.6 |
| | 500 | 0.4 |
| Thrombin + HV1C3 (10 NIH unit/10 g weight) | 20 | 1.2 |
| | 50 | 0.6 |
| | 100 | 0.4 |

*Score
score 0: no disappearance of roll over reflection (apparently normal)
score 1: disappearance of roll over reflection, but no death within 20 minutes
score 2: death within 20 minutes As is clear from the table, in the thrombin induced death reaction in vivo, chimeric hirudin (HV1C3) of the present invention exhibited about 4–5 times greater inhibitory activity compared with hirudin HV1.

EXAMPLE 3

Prolongation of bleeding time

Samples were injected into male mice (20–25 g) under anesthesia using sodium pentobarbital (40 mg/kg i.p.) via their tail vein. A puncture wound was made by inserting a 21 G needle (outer diameter 0.85 mm) into the other side of the tail vein 5 minutes after the administration of the test compounds, and the bleeding time of the wound was measured. A filter paper was put on the wound, with changes every 15 seconds. Bleeding time is defined as the time required until no red spot is observed on the filter paper. The results are shown in Table 6.

TABLE 6

Prolongation of bleeding time

| Tested compound | Amount administered (μg/10 g weight) | Bleeding time (sec) |
|---|---|---|
| Saline | | 148.5 ± 14.6 |
| HV1 | 20 | 223.7 ± 15.6 |
| | 50 | 376.7 ± 20.2 |
| | 100 | 501.7 ± 47.1 |
| HV1C3 | 50 | 264.0 ± 17.6 |
| | 100 | 291.0 ± 30.2 |
| | 200 | 369.0 ± 34.9 |

In general, prolongation of bleeding time is one of the side effects of anti-coagulants. Hem, the chimeric hirudin (HV1C3) of the present invention was clearly confirmed to cause less bleeding than hirudin HV1.

EXAMPLE 4

Preparation having chimeric hirudin HV1C3 as an ingredient

The purified chimeric hirudin HV1C3 of the Example 1-(9) was desalted using Sephadex G25 (Pharmacia), followed by filtering through a 0.22 μm filter under sterile conditions. The solution was dispensed into vials and lyophilized. The thus obtained lyophilized powder of chimeric hirudin HV1C3 can be dissolved in saline and used as an injectable drug.

EXAMPLE 5

Production of hirudin HV3

Figure 9:
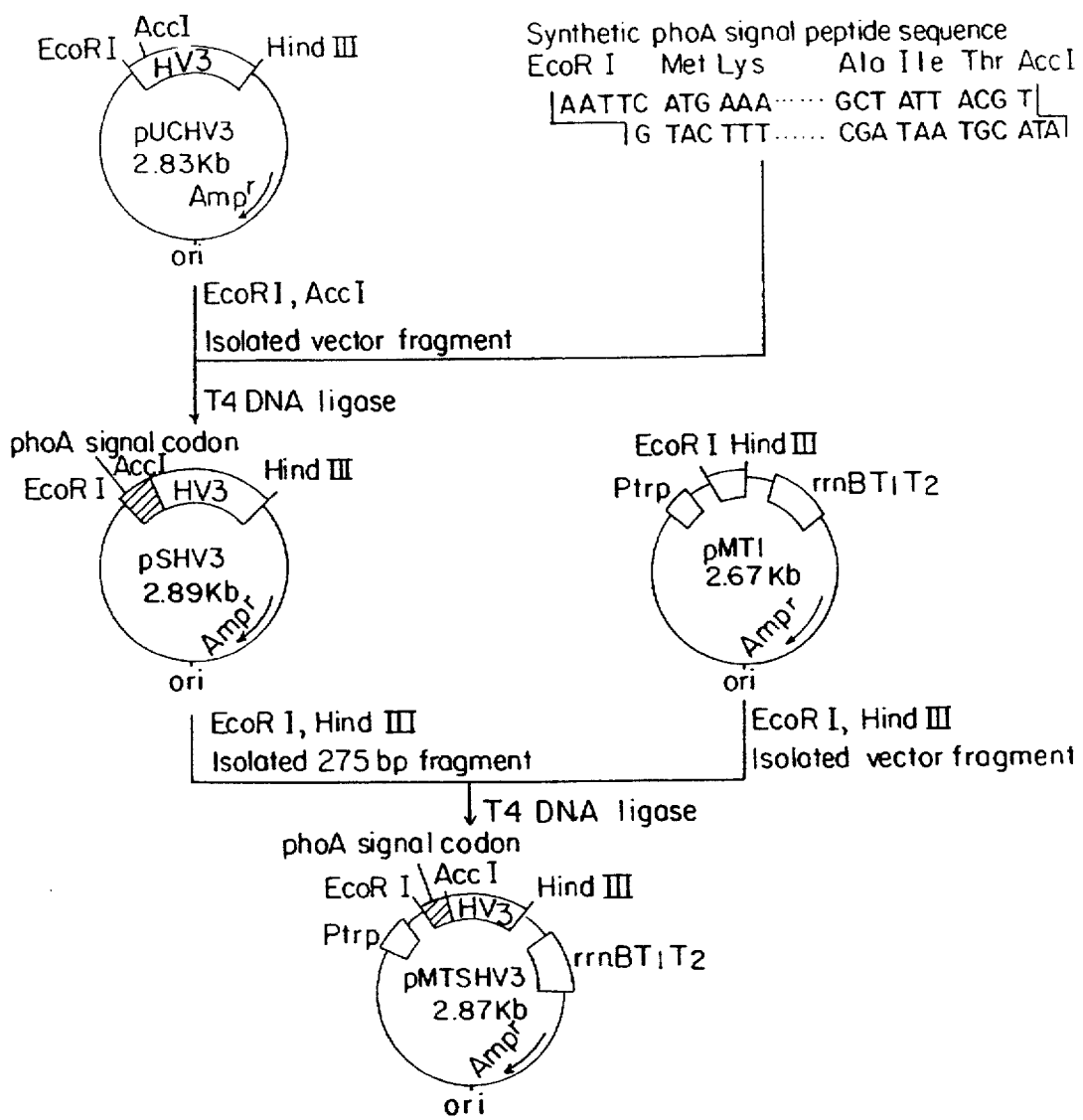
FIG. 9 shows an outline of the construction of hirudin HV3 secreting plasmid pMTSHV3.

(1) Construction of a hirudin HV3 secretion plasmid (i) As shown in FIG. 9, the replication origin (ori) obtained by digesting the plasmid pUCHV3 prepared in reference example 1 with restriction enzymes EcoRI and AccI, a vector fragment including the ampicillin resistance gene, and a synthetic gene encoding the signal sequence of alkaline phosphatase (phoA), the DNA sequence of which is shown in FIG. 10, were ligated using T4 DNA ligase. As a result, plasmid pSHV3 was obtained, in which the DNA sequence encoding the signal peptide of the alkaline phosphatase gene (phoA) was joined upstream from the DNA sequence encoding HV3. The plasmid was introduced into E. coli JM109, followed by culturing and screening for ampicillin resistance.

(ii) Next, plasmid pSHV3 was cleaved with restriction enzymes EcoRI and HindIII to obtain a 275 bp gene fragment having a DNA sequence encoding the signal peptide of the alkaline phosphatase gene (phoA) joined upstream from the DNA sequence encoding HV3.

(iii) On the other hand, plasmid pMT1 was prepared by the method described in reference example 2. This plasmid comprises a DNA sequence including the replication origin (ori) of plasmid pUC18 and the trp promoter as described in reference example 2. The vector fragment was obtained by cleaving plasmid pMT1 with the restriction enzymes EcoRI and HindIII.

(iv) The aforesaid 275 bp fragment and the vector fragment were ligated using T4 DNA ligase, introduced into E. coli JM109, which was cultured, and screened for ampicillin resistance to obtain plasmid pMTSHV3, the 2.87 kb HV3 expression vector which comprises a DNA sequence including the replication origin (ori) of plasmid pUC, the DNA sequence of the trp promoter, a DNA sequence encoding the signal peptide of the alkaline phosphatase gene (phoA), and the DNA sequence encoding HV3.

(2) Secretion production of hirudin HV3 by the hirudin HV3 secretion plasmid

E. coli RR1 (E. coli RR1/pMTSHV3) (FERM BP-3267), transformed with plasmid pMTSHV3 which was constructed by the above described method, was cultured in 2 L of 2×YT medium containing 100 μg/ml ampicillin and 2% glucose. Culturing was carried out in 2 L of medium in a 5 L jar at 37° C. for 24 hours. As a result, 6073 ATU of anti-thrombin activity per 1 ml of culture medium were detected.

(3) Purification of hirudin HV3 from culture media

Hirudin HV3 was obtained from the culture medium by the method described in Example 1-(5). Specifically, after the culture medium was centrifuged to separate the supernatant from the cells, the supernatant was diluted 4-fold with 10 mM potassium phosphate buffer (pH7.0) and filtered. The obtained filtrate was loaded on a column (4.4×13 cm) of QAE-toyopearl as described in example (5), followed by gel filtration on a Sephacryl S-100HR column.

Figure 11:
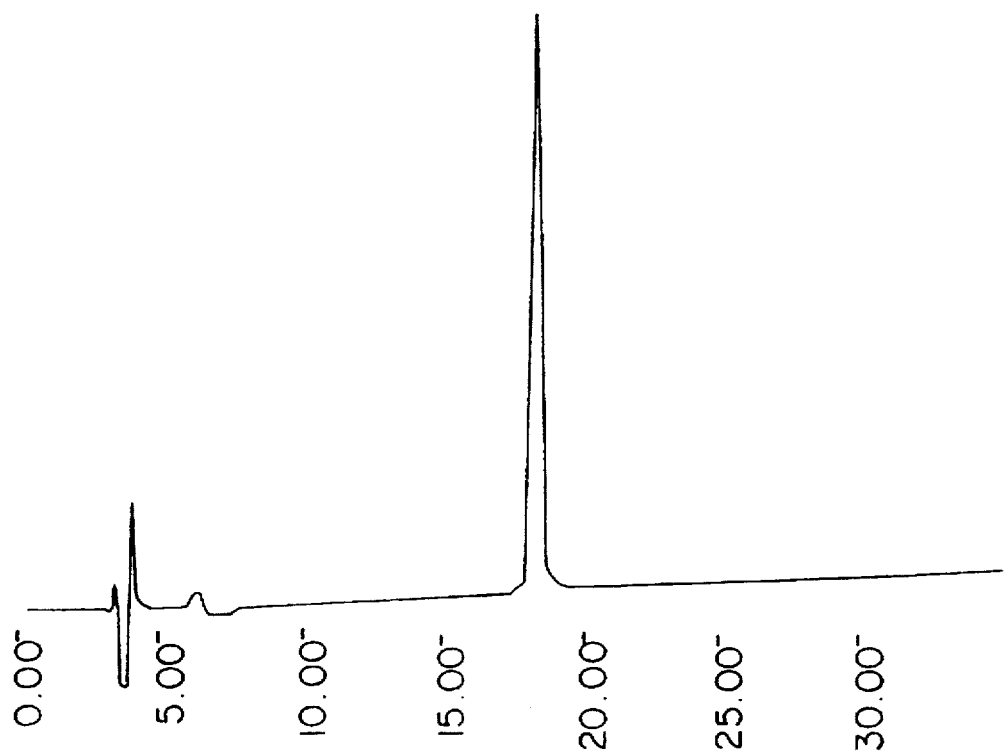
FIG. 11 shows the profile of purified hirudin HV3 by C4 reverse phase HPLC.

The active fraction was loaded on a column of DEAE toyopearl (4.4×40 cm) equilibrated with equilibration buffer and then eluted with a linear gradient from 0 to 0.3M NaCl in equilibration buffer. Finally, hirudin HV3 was purified by C4 reverse HPLC using a Vydac C4 column (4.7×30 cm) eluted with a linear gradient (1%/min, 30 min or longer) of acetonitrile from 15 to 30% (v/v). The profile is shown in FIG. 11.

The degree of purification of each step is shown in Table 7.

TABLE 7

| Purification step | Total protein (mg) | Total activity (ATU) | Relative activity (ATU/mg) | Recovery (%) |
|---|---|---|---|---|
| culture medium | 15600 | 11034400 | 707 | 100 |
| QAE-toyopearl | 2111 | 9227264 | 4371 | 83.6 |
| S-100HR | 1453 | 9268963 | 6381 | 84.0 |
| DEAE-toyopearl | 1327 | 8597892 | 6478 | 77.9 |
| C4-HPLC | 795 | 6486480 | 8139 | 58.8 |

When the amino acid composition and N-terminal amino acid sequence of the purified product were analyzed, the amino acid composition exhibited a value consistent with the theoretical value of hirudin HV3 as shown in Table 8. As shown in Table 9, the sequence up to the 15th amino acid of the N-terminal amino acid sequence was identical with that of hirudin HV3. These results evidence the correct processing of the signal peptide, and the product was confirmed to be hirudin HV3.

TABLE 8

|  | HV3 | Theoretical |
|---|---|---|
| Asx | 9.76 | 10 |
| Thr | 4.74 | 5 |
| Ser | 3.68 | 4 |
| Glx | 11.55 | 11 |
| Gly | 8.77 | 9 |
| Ala | 1.07 | 1 |
| Cys | 5.22 | 6 |
| Val | 2.03 | 2 |
| Met | 0.00 | 0 |
| Ile | 2.97 | 3 |
| Leu | 3.08 | 3 |
| Tyr | 2.04 | 2 |
| Phe | 1.00 | 1 |
| His | 1.22 | 1 |
| Lys | 4.03 | 4 |
| Arg | 0.00 | 0 |
| Pro | 4.06 | 4 |
| Total |  | 66 |

TABLE 9

| Cycle number | Amino acid | Yield (pmol) |
|---|---|---|
| 1 | Ile | 469 |
| 2 | Thr | 108 |
| 3 | Tyr | 106 |
| 4 | Thr | 102 |
| 5 | Asp | 122 |
| 6 | Cys | — |
| 7 | Thr | 100 |
| 8 | Glu | 76 |
| 9 | Ser | 32 |
| 10 | Gly | 172 |
| 11 | Gln | 145 |
| 12 | Asn | 93 |
| 13 | Leu | 211 |
| 14 | Cys | — |
| 15 | Leu | 189 |

INDUSTRIAL APPLICABILITY

The present invention provides a new hirudin analog. The hirudin analog of the present invention is useful as an anti-coagulant having strong anti-thrombin activity and a reduced tendency to cause bleeding.

Also, the present invention provides secretion vectors for secretion of foreign proteins including the aforesaid hirudin analog, transformed microorganisms, and methods of manufacturing foreign proteins using said transformed microorganisms. Using the method described in the present invention, foreign proteins can be produced extracellularly in high yield, which is industrially advantageous for obtaining foreign proteins.

Deposits of microorganisms:

(1) *E. coli* JM109/pMTSHV1C3 (Entry *E. coli* JM109/pMTPHOHV1C3 was amended)
  Deposit Organization:
  Fermentation Research Institute,
  Agency of Industrial Science and Technology,
  Ministry of International Trade and Industry
  Address:
  1-1-3, Tsukuba-shi Higashi, Ibaraki-ken, Japan
  Date of Deposit:
  Sep. 18, 1990
  Deposit Number:
  FERM BP-3104

(2) *E. coli* RR1/pMTSHV1C3
  Deposit Organization:
  Fermentation Research Institute,
  Agency of Industrial Science and Technology,
  Ministry of International Trade and Industry
  Address:
  1-1-3, Tsukuba-shi Higashi, Ibaraki-ken, Japan
  Date of Deposit:
  Oct. 11, 1990
  Deposit Number:
  FERM BP-3130

(3) *E. coli* JM109/pMTSHV1
  Deposit Organization:
  Fermentation Research Institute,
  Agency of Industrial Science and Technology,
  Ministry of International Trade and Industry
  Address:
  1-1-3, Tsukuba-shi Higashi, Ibaraki-ken, Japan
  Date of Deposit:
  Feb. 6, 1991
  Deposit Number:
  FERM BP-3266

(4) *E. coli* RR1/pMTSHV3
  Deposit Organization:
  Fermentation Research Institute,
  Agency of Industrial Science and Technology,
  Ministry of International Trade and Industry
  Address:
  1-1-3, Tsukuba-shi Higashi, Ibaraki-ken, Japan
  Date of Deposit:
  Feb. 6, 1991
  Deposit Number:
  FERM BP-3267

We claim:

1. A hirudin analog, HV1C3, having the amino acid sequence of SEQ ID NO:1.

2. A DNA sequence encoding the amino acid sequence of SEQ ID NO:1 of claim 1.

3. A transformed microorganism, obtained by transforming E. coli with an expression vector containing a DNA sequence encoding said amino acid sequence of SEQ ID NO:1 of claim 1 operably linked thereto.

4. A method of manufacturing hirudin analog HV1C3 having the amino acid sequence of SEQ ID NO.:1, comprising culturing said transformed microorganism of claim 3, expressing said hirudin analog HV1C3, and recovering said hirudin analog HV1C3.

5. A secretion vector, comprising a DNA sequence comprising a replication origin of a pUC plasmid, a tac or a trp promoter, a DNA sequence encoding a signal peptide, and a DNA sequence encoding hirudin analog HV1C3 having the amino acid sequence of SEQ ID NO:1 linked directly downstream from said DNA sequence encoding said signal peptide, all linked in an operable manner.

6. An anti-coagulation drug having hirudin analog HV1C3 according to claim 1 as an active ingredient.

7. The DNA sequence according to claim 2, having the sequence of SEQ ID NO:2.

8. The secretion vector according to claim 5, wherein said secretion vector is pMTSHV1C3.

9. The secretion vector according to claim 5, wherein said DNA sequence encoding said signal peptide encodes an alkaline phosphatase signal peptide.

10. The secretion vector according to claim 5, wherein said DNA sequence of said replication origin of said pUC plasmid is obtained by digesting plasmid pUC18 with the restriction enzymes PvuI and PvuII.

\* \* \* \* \*

UNITED STATES PATENT AND TRADEMARK OFFICE
CERTIFICATE OF CORRECTION

PATENT NO. : 5,516,656
DATED      : May 14, 1996
INVENTOR(S): Misawa et al

It is certified that error appears in the above-indentified patent and that said Letters Patent is hereby corrected as shown below:

On the title page: Item

[73] Assignee:" change

"Nippon Mining Company, Limited" to --Japan Energy Corporation--.

Signed and Sealed this

Tenth Day of December, 1996

Attest:

BRUCE LEHMAN

*Attesting Officer*     *Commissioner of Patents and Trademarks*